ated Jun. 15, 2009 (12 pages.)

(12) United States Patent
Petersen et al.

(10) Patent No.: US 8,068,917 B2
(45) Date of Patent: Nov. 29, 2011

(54) FAIL-SAFE PROGRAMMING FOR IMPLANTABLE MEDICAL DEVICE

(75) Inventors: Christopher M. Petersen, Ham Lake, MN (US); James E. Willenbring, St. Paul, MN (US)

(73) Assignee: Medtronic, Inc., Minneapolis, MN (US)

( * ) Notice: Subject to any disclaimer, the term of this patent is extended or adjusted under 35 U.S.C. 154(b) by 771 days.

(21) Appl. No.: 10/650,946

(22) Filed: Aug. 29, 2003

(65) Prior Publication Data

US 2005/0049656 A1  Mar. 3, 2005

(51) Int. Cl.
*A61N 1/37* (2006.01)
(52) U.S. Cl. .......................................... 607/60; 607/31
(58) Field of Classification Search .................. 607/60, 607/31
See application file for complete search history.

(56) References Cited

U.S. PATENT DOCUMENTS

| | | | | |
|---|---|---|---|---|
| 5,113,869 | A * | 5/1992 | Nappholz et al. | 600/508 |
| 5,456,692 | A | 10/1995 | Smith, Jr. et al. | 607/31 |
| 5,899,931 | A | 5/1999 | Deschamp et al. | 607/60 |
| 6,416,471 | B1 | 7/2002 | Kumar et al. | 600/300 |
| 2001/0031998 | A1 * | 10/2001 | Nelson et al. | 607/60 |
| 2001/0041920 | A1 * | 11/2001 | Starkweather et al. | 607/60 |
| 2002/0013518 | A1 | 1/2002 | West et al. | 600/300 |
| 2002/0049480 | A1 * | 4/2002 | Lebel et al. | 607/60 |
| 2002/0147473 | A1 * | 10/2002 | Seim et al. | 607/14 |
| 2003/0050535 | A1 | 3/2003 | Bowman, IV et al. | 600/300 |

OTHER PUBLICATIONS

International Search Report from corresponding PCT Application Serial No. PCT/US2004/027957 mailed Jan. 28, 2005 (10 pages).
Written Opinion from corresponding PCT Application Serial No. PCT/US2004/027957 mailed Jan. 28, 2005 (7 pages).
International Preliminary Report on Patentability from corresponding PCT Application Serial No. PCT/US2004/027957 mailed Feb. 28, 2006 (8 pp.).
European Office Action from corresponding European Application No. 04 782 439.6 dated Jan. 26, 2009 (2 pages.)
Response to European Office Action from corresponding European Application No. 04 782 439.6 dated Jul. 15, 2009 (12 pages.)
European Office Action from corresponding European Application No. 04 782 439.6 dated Dec. 3, 2009 (3 pages.)

* cited by examiner

*Primary Examiner* — Michael Kahelin

(57) ABSTRACT

In general, the invention is directed to a system with a fail-safe mode for remote programming of medical devices, such as implantable medical devices (IMDs). During a remote programming session, an adverse event, such as a programming session failure, may prevent proper completion of a programming or result in improper programming due to data corruption or other factors. If a programming session is not completed correctly, the IMD is susceptible to improper operation, possibly exposing a patient to delivery of unnecessary or inappropriate therapies. A fail-safe mode reduces the likelihood of improper operation following a programming session failure. The fail-safe mode defines one or more fail-safe operations designed to preserve proper operation of the IMD. In some embodiments, the fail-safe operations include notifying a person concerning the failure of the programming session, modifying programming parameters within the implantable medical device, and delivering a therapy to a patient.

15 Claims, 5 Drawing Sheets

FAIL-SAFE PROGRAMMING FOR IMPLANTABLE MEDICAL DEVICE

TECHNICAL FIELD

The invention relates to implantable medical devices, and more particularly, to techniques for remote programming of implantable medical devices.

BACKGROUND

Implantable medical device (IMD), such as implantable pacemakers, cardioverter/defibrillators, neurostimulators, implantable drug pumps, or the like, may be programmed and interrogated remotely via a telecommunication link. In particular, a remote programmer initiates a remote programming session to set parameters within the IMD and thereby modify therapy or monitoring for a patient. The programming session may involve a local programmer/monitor, located proximate to the patient, that acts as an intermediary between the remote programmer and the IMD.

Remote programming allows a programmer to program an IMD from a significant distance. A doctor may monitor the programming from any location that is able to access the same network to which the IMD is connected, e.g., the Internet. In this manner, remote programming should make patient visits to the clinic less frequent. Remote programming of implantable medical devices is likely to become more prevalent as technology to enable safe remote implementation emerges.

SUMMARY

In general, the invention is directed to a system with a fail-safe mode for remote programming of medical devices, such as implantable medical devices (IMDs). During a remote programming session, an adverse event, such as a programming session failure, may prevent proper completion of a programming or result in improper programming due to data corruption or other factors. If a programming session is not completed correctly, the IMD is susceptible to improper operation, possibly exposing a patient to delivery of unnecessary or inappropriate therapies.

In accordance with the invention, a fail-safe mode reduces the likelihood of improper operation following a programming session failure. The fail-safe mode defines one or more fail-safe operations designed to preserve proper operation of the IMD. In some embodiments, the fail-safe operations include notifying a person concerning the failure of the programming session, modifying programming parameters within the implantable medical device, and delivering a therapy to a patient. As one example, the fail-safe mode may cause the IMD to revert to a default set of programming parameters in the event the programming session fails.

In one embodiment, the invention is directed to a method comprising initiating a remote programming session within an implantable medical device, and invoking a fail-safe operation in the event the programming session fails.

In another embodiment, the invention is directed to a method comprising initiating a remote programming session within an implantable medical device, and reverting to default programming parameters within the implantable medical device if the remote programming session results in inappropriate operation of the implantable medical device.

In another embodiment, the invention is directed to an implantable medical device comprising a communication interface for initiation of a remote programming session, and a processor that invokes a fail-safe operation in the event the programming session fails.

In another embodiment, the invention is directed to a local programmer of an implantable medical device system comprising a communication interface for initiation of a remote programming session, and a processor that invokes a fail-safe operation in the event the programming session fails.

In another embodiment, the invention is directed to a remote programmer for an implantable medical device, the programmer comprising a communication interface for initiation of a remote programming session with the implantable medical device, and a processor that invokes a fail-safe operation in the event the programming session fails.

In another embodiment, the invention is directed to a system comprising an implantable medical device, a local programmer that programs the implantable medical device, a remote programmer that communicates with the local programmer to initiate a remote programming session with the implantable medical device, and a processor that invokes a fail-safe operation in the event the programming session fails.

In other embodiments, the invention is directed to computer-readable media comprising instructions to cause a processor to implement methods as described herein The details of one or more embodiments of the invention are set forth in the accompanying drawings and the description below. Other features, and aspects of the invention will be apparent from the description and drawings, and from the claims.

DETAILED DESCRIPTION

The invention pertains to remote programming of an implantable medical device (IMD). During a remote programming session, an adverse event, such as a communication failure, may prevent the proper completion of programming or result in improper programming due to data corruption or other factors. To combat adverse events, the invention provides a fail-safe mode, which may include notifying a person concerning the failure of the programming session, modifying programming parameters within the implantable medical device, or delivering a therapy to a patient.

Figure 1:
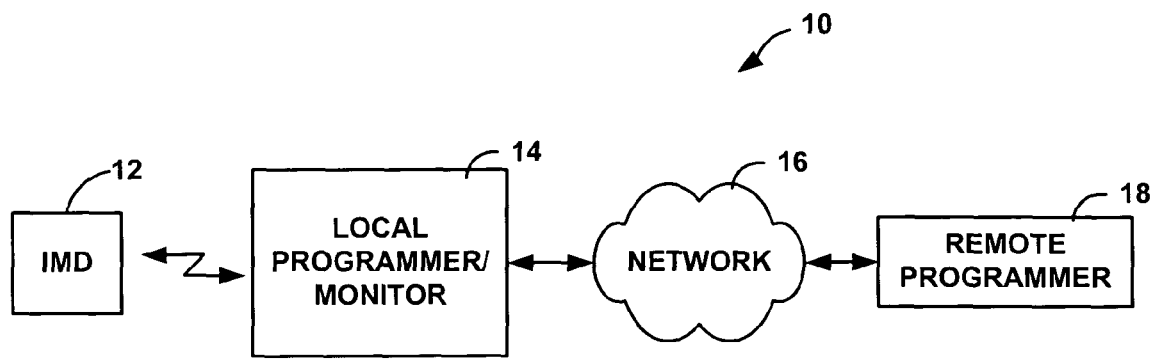
FIG. 1 is a block diagram illustrating an exemplary implantable medical device system that provides a fail-safe mode for remote programming.

FIG. 1 is a block diagram illustrating an exemplary implantable medical device system 10 that provides a fail-safe mode in the event an adverse event occurs in the course of a remote programming session. As shown in FIG. 1, system 10 includes an implantable medical device (IMD) 12, a local programmer/monitor 14, and a remote programmer 18. Remote programmer 18 communicates with local programmer/monitor 14 via a network 16, which may include the Internet, LANs, WANs, wireless networks, cellular networks, satellite networks, VPNs, and the like.

Local programmer/monitor 14 communicates with IMD 12 via short-range or longer-range wireless telemetry. For example, local programmer/monitor 14 may include a programming/interrogation wand for short-range telemetry with IMD 12, or a radio frequency antenna for longer range telemetry with the IMD. IMD 12 may be an implantable pacemaker, a cardioverter/defibrillator, a neurostimulator, an implantable drug pump, an implantable monitor, or the like.

Local programmer/monitor 14 sets operating parameters within IMD 12 to control therapy for a patient and monitor patient response to the therapy. Remote programmer 18 initiates a remote programming or monitoring session with IMD 12 via local programmer/monitor 14 via network 16, and the local programmer/monitor then programs and interrogates the IMD via local telemetry.

Remote programmer 18 relies on an array of intermediate networking equipment along a telecommunication link, including network 16, to communicate with local programmer/monitor 14 and IMD 12. The intermediate networking equipment, such as routers, servers, hubs, and the like, as well as software, such as web browsers, drivers, and other communication and rendering modules, may create potential faults, outages and other adverse events within the telecommunication link.

In general, the conglomeration of equipment and software along the telecommunication link creates an unpredictable, hazardous environment that presents reliability issues in the remote programming context. Transmission failures and data corruption are two possible effects of a hazardous environment. However, the sensitive nature of IMDs requires stability of a controlled operating environment to promote viability of remote programming.

Remote programming is further complicated by telemetry between local programmer/monitor 14 and IMD 12. As a result, a remote programming session may encounter an adverse event due to not only a failure in the telecommunication link between remote programmer 18 and local programmer/monitor 14, but also a failure in the telemetry link between local programmer/monitor 14 and IMD 12, e.g., due to interference or out-of-range conditions. In either case, an adverse event may result in a programming session failure, inappropriate device behavior, or inappropriate patient response to improper parameters.

As discussed above, a programming session failure includes a disruption in telemetry between IMD 12 and local programmer/monitor 14 located proximate the implantable medical device, a disruption in a telecommunication link between the local programmer/monitor 14 and remote programmer 18, a loss of connection between clinician instrumentation and remote programmer 18, or the like, and results in incomplete or improper programming. For example, a connection may be lost between two devices if a power interruption occurs. In addition, a connection may be lost if a device is out of range, or if the device suffers interference.

Inappropriate device behavior includes programming of inappropriate parameters due to inadvertent programming by the clinician or other medical personnel, incomplete programming, power interruptions, or corruption of data or instructions. Further, inappropriate device behavior includes improper operation by IMD 12, such as the occurrence of an asystole by IMD 12, inappropriate IMD sensitivity settings, inappropriate AV delay settings, inappropriate refractory period settings, inappropriate pacing and defibrillation output settings and the like.

Inappropriate patient response, caused by inappropriate operation of IMD 12, include low pacing outputs, low pacing rate, loss of capture, loss of sensing or monitoring, loss of defibrillation efficacy, arrhythmia, and the like, in response to therapy delivery by IMD 12 based on the programmed parameters.

Fail-safe operations prevent harmful consequences from inappropriate programming caused by an adverse event during remote programming, as described above. Fail-safe operations include notifying a person concerning the failure of the programming session, modifying or maintaining programming parameters within the implantable medical device, delivering a therapy to a patient, or a combination of such operations. Notification of programming session failure permits the patient to seek medical attention immediately, and may take the form of an audible, visible or tactile notification.

Modifying programming parameters permits restoration of IMD 12 to previous settings or limitation of programming parameters to applicable safety margins, and may involve causing the IMD to revert to a default set of programming parameters in the event the programming session fails. Delivery of therapy, either from the IMD or an external device such as an automated external defibrillator, external drug pump, or the like, maintains the patient's condition until medical help can be obtained.

An example scenario may involve a first parameter setting, which may be reprogrammed to a second parameter setting. For example, the first parameter setting may provide for DDD pacing, and the second parameter setting may provide AAI, which leads to no ventricular pacing. If a programming session fails, the parameters in IMD 12 may be restored to provide for DDD pacing. In another embodiment, "safe mode" parameters may be set if they were passed to IMD 12 during initialization of the programming session. For example, IMD 12 may limit the programming, allowing only modes that support ventricular pacing.

Figure 2:
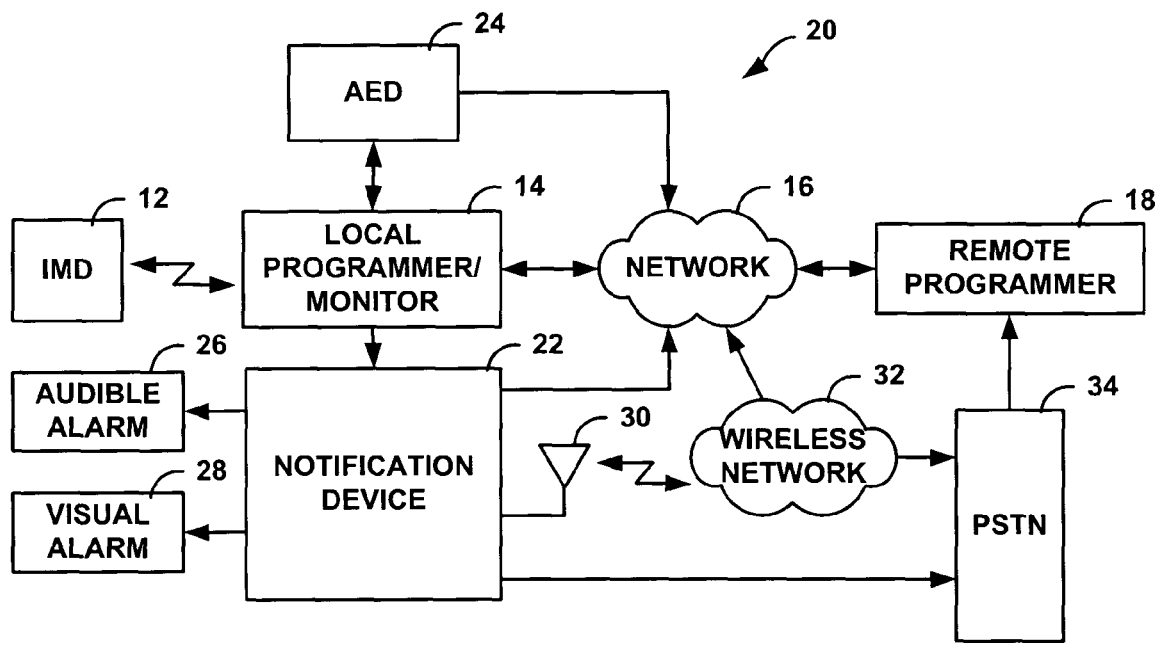
FIG. 2 is a block diagram illustrating the system of FIG. 1 in greater detail.

FIG. 2 is a block diagram illustrating an exemplary implantable medical device system 20 that implements fail-safe operations. FIG. 2 illustrates details of a particular implementation of IMD system 10 shown in FIG. 1. Accordingly, IMD system 20 may include the components of IMD system 10 as well as other devices that contribute to one or more fail-safe operations incident to a remote programming session. As shown in FIG. 2, IMD system 20 includes IMD 12, local programmer/monitor 14, network 16 and remote programmer 18. Local programmer/monitor 14 either includes or interacts with a notification device 22 that generates a notification in response to an adverse event incident to a remote programming session.

Notifying a person concerning the failure of the programming session includes notifying a clinician or the patient by generating a visible, audible or tactile notification, sending an electronic message, sending a postal mail letter, or the like. A notification device 22 provides the functionality for notifying a person concerning the failure of the programming session. In one embodiment, notification device 22 is located within local programmer/monitor 14. In particular, an audible alarm 26 or a visual alarm 28 may be located within or coupled to notification device 22, thereby providing a notification to the patient.

In another embodiment, notification device 22 is located within IMD 12 and is responsive to a programming session failure to provide an audible notification in the form of an alarm via a speaker provided in the IMD, or a tactile notification in the form of a vibration via a vibrating element provided in the IMD. Other notifications, such as fragrances, stimulation shocks, or the like may be emitted by a notification device within local programmer/monitor 14 or IMD 12 to alert the patient to the failure of a programming session.

In other embodiments, notification device 22 sends an electronic message as a notification, either to a patient or health care personnel, or both. The electronic message includes one of a short messaging service (SMS) message, an instant messenger message, an email, an audible alert on a remote programmer, a visual alert on a remote programmer, an audible alert on a wireless device, a visual alert on a wireless device, and the like.

Notification device 22 sends the notification via network 16, wireless network 32, or via Public Switched Telephone Network (PSTN) 34. An antenna 30 enables a notification device 22 to communicate with wireless network 32. A connection with wireless network 32 allows communication with remote programmer 18 via PSTN 34 or network 16. In one embodiment, notification device 22 communicates directly via network 16.

In some embodiments, remote programmer 18 provides a notification to health care personnel, such as clinician, co-located with the remote programmer. For example, remote programmer 18 may integrate or be coupled to a notification device that notifies the health care personnel of a programming failure in the event network communications fail. Remote programmer 18 detects communication failure, for example, in response to a timeout following a previous communication with receiving an acknowledgement or other reply from network equipment between the remote programmer and local programmer/monitor 14.

In each case, notification device 22 sends a notification to remote programmer 10. In particular, PSTN 34 relays information about an adverse event or a parameter setting of IMD 12, enabling a clinician or other health care personnel to take appropriate action. In addition, as mentioned above, notification device 22 may send an electronic message to a device associated with the patient, such as a handheld computing device, handheld programmer device, cellular telephone, or pager.

In addition to sending a notification, another fail-safe operation involves modifying programming parameters within the IMD 12. For example, upon detection of an adverse event such as a programming session failure due to a telecommunication link failure, local programmer/monitor 14 instructs IMD 12 to revert to a set of default parameters, rather than operate according to any parameters that may have been loaded as a result of the programming session.

As an alternative, IMD 12 may automatically revert to a set of default parameters in the event the local telemetry link fails or local programmer/monitor 14 indicates that the telecommunication link has failed. Detection of programming session failure may be based on detection of an interruption of communication, failure to receive an end of programming verification such as a commit command or signal, receipt of a specific error signal, or other events.

The default parameters ensure at least basic operation of IMD 12 to preserve patient health, while avoiding potentially hazardous device settings that may result from incomplete programming or corruption of instructions or data. A memory module within IMD 12 or local programmer/monitor 14 stores previous parameter settings, such as default parameters for use in a fail-safe mode. In the event IMD 12 is configured to detect a failure of the programming session, the default parameters preferably are stored within a memory module in IMD 12.

As a further alternative, local programmer/monitor 14 may be configured to transmit modified programming parameters to IMD 12 in the event an adverse event such as a programming session failure is detected. Instead of causing IMD 12 to revert to a set of default parameters, local programmer/monitor 14 modifies some of the program parameters so that they reside within a conservative safety range established for the particular IMD 12 and patient.

Local programmer/monitor 14 also may be configured to delivery a therapy in response to an adverse event associated with remote programming. Delivering therapy to a patient, another fail-safe operation, may include therapy delivered via one of an automated external defibrillator (AED) 24, an external drug pump, an external neurostimulator, IMD 12, or other devices. For example, AED 24 may be integrated with remote programmer 18 to monitor patient data, such as an electrocardiogram (ECG), and provide therapy if IMD 12 is not already providing appropriate therapy. In particular, AED 24 provides a fail-safe mode under control of local programmer/monitor 14, e.g., if the patient experience fibrillation due to improper operation of IMD 12 or during a period in which IMD 12 is unable to respond to the fibrillation due to improper programming.

Another example of delivering therapy includes a drug pump that is directed to release a prescribed amount of a medication in accordance with a detected adverse event, e.g., under control of local programmer/monitor 18. Similarly, local programmer/monitor 18 may control other types of devices such as neurostimulator to deliver therapy in the event IMD 12 operates improperly. Alternatively, in some embodiments, local programmer/monitor 18 presents visible or audible instructions to the patient to indicate a suggested therapy for self-administration by the patient.

In some embodiments, IMD 12 is configured to deliver therapy if an adverse event is detected as a result of a remote programming session. For example, IMD 12 may deliver particular pacing therapies in response to detection of an adverse event. IMD 12 may deliver the therapies in response to notification of an adverse event by notification device 22 or local programmer/monitor 14. The particular therapy available to the patient can be specific to IMD 12, the patient, the clinician, the location of the patient or clinician, or other criteria.

In a further embodiment, a failure log is maintained within local programmer/monitor 14, remote programmer 18, or IMD 12. The failure log provides information about the occurrence of adverse events in the course of a remote programming session. In this manner, the failure log aids the clinician in identifying improper programming states of IMD 12, as well as trouble-shooting potential sources of programming session failures, such as components or software implicated in communication via a telecommunication or telemetry link.

Figure 3:
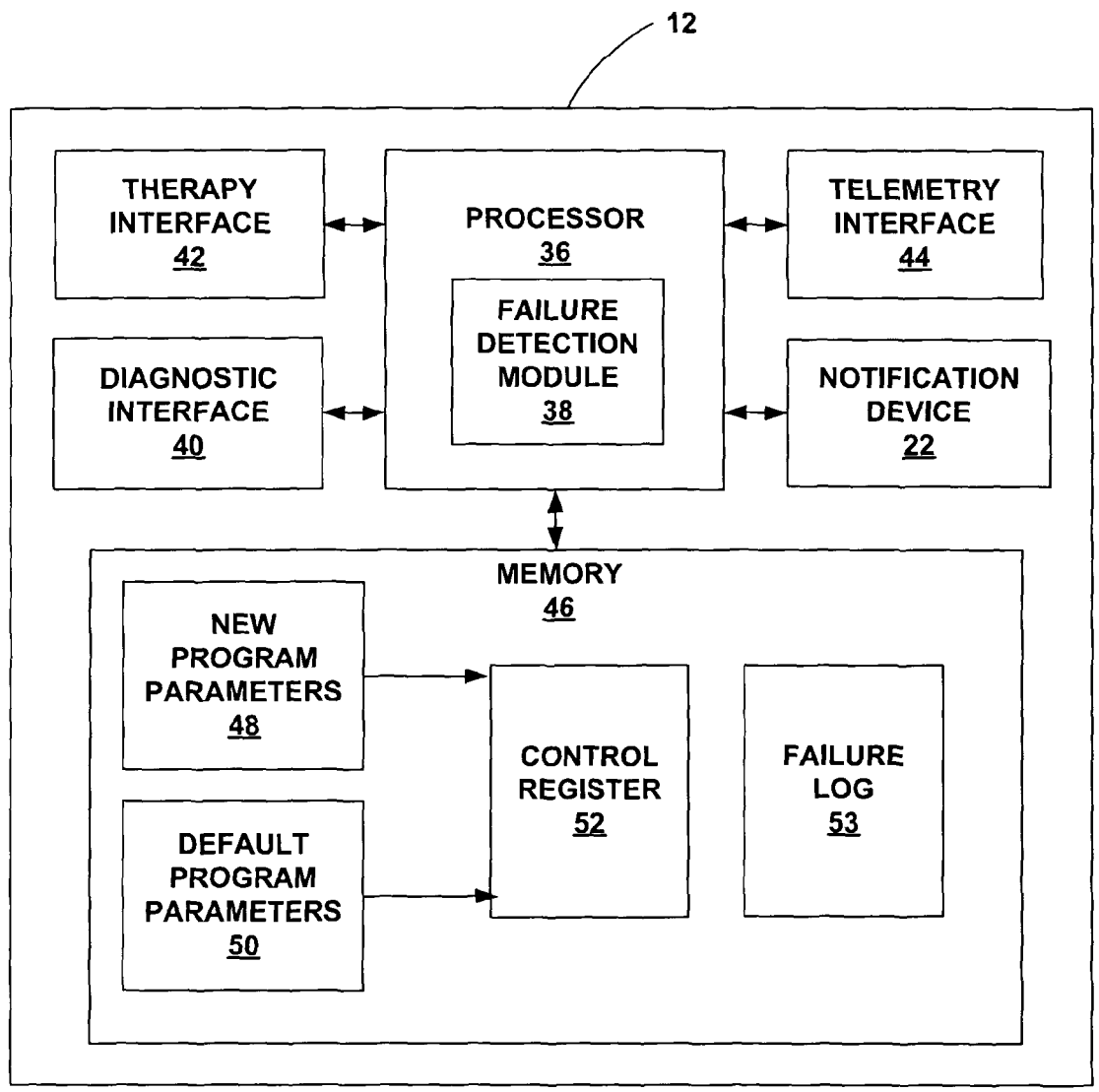
FIG. 3 is a conceptual diagram illustrating an exemplary implantable medical device (IMD) that provides fail-safe operations if an adverse event occurs.

FIG. 3 is a conceptual diagram illustrating an exemplary implantable medical device (IMD) 12 that provide fail-safe operations in response to an adverse event associated with remote programming. As shown in FIG. 3, IMD 12 includes a processor 36 that executes a failure detection module 38 to detect adverse events relating to remote programming. IMD 12 further includes a diagnostic interface 40 to sense physiological parameters within the patient, and a therapy interface 42 to deliver therapy such as electrical stimulation or drug administration. IMD 12 also includes a telemetry interface for communication with local programmer/monitor 14 or a programmer in a clinician's office. In some embodiments, IMD 12 includes an internal notification device 22 to notify the patient of an adverse event, e.g., by audible or tactile notification.

IMD 12 includes components that aid in detection of adverse events and defense against adverse events. Processor 36 detects either programming session failure or notifications of programming session failures, and invokes fail-safe operations by other components of the IMD. For example, failure detection module 38, executed within processor 36, may detect an adverse event, such as a programming session failure between telemetry interface 44 and a programmer. Processor 36 then directs an appropriate fail-safe operation in response to an adverse event.

A memory 46 stores new program parameters 48, default program parameters 50, a control register 52 and a failure log 53. Accordingly, memory 46 separates new program parameters received in the course of a remote programming session from default program parameters, which are persistently stored in the event of usage following detection of an adverse event. In particular, processor 36 loads control register 52 with new program parameters 48 if the remote programming session is successful, but loads control register 52 with the default program parameters 50 if failure of the remote programming session is detected. IMD 12 then operates according to the parameters loaded in control register 52. Failure log 53 logs information concerning detection of adverse events associated with remote programming sessions. The information logged by failure log 53 may be sent to a device such as remote programmer 18.

In another embodiment, a first parameter setting is reprogrammed for a specific period of time to a second parameter setting, after which the first setting may be restored automatically. This "test mode" embodiment may be useful in testing situations, in which it is not desired to have the second parameter setting be permanent. In an alternative embodiment, a series of parameter changes are programmed to be set in a sequence at predetermined intervals. If IMD 12 detects a programming failure at any point in a series of parameter changes, IMD 12 can restore the first parameter setting or maintain the second parameter setting if the second parameter setting is still appropriate for the condition of the patient. The "test mode" parameters may be stored in new program parameters register 48 or default program parameters register 50, and be passed to control register 52 as directed by processor 36.

In a further embodiment, parameters may be queued in new program parameters register 48 while activation of a programmed parameter is delayed intentionally. After the delay has been accomplished, the condition of the patient may be monitored to verify that the programmed parameter is appropriate. The new programmed parameter setting may be aborted in favor of a default parameter setting if the changes are not appropriate for the condition of the patient.

Alternatively or, in addition, processor 36 notifies the patient concerning the failure of the programming session via notification device 22. Notification device 22 may emit include a vibration, a sound, or an electrical stimulation. Alternatively, notification device may send a message to an external device via telemetry interface 44 to cause the device to emit a visible or audible notification, a voice prompt, a fragrance, an electronic message, and the like. Again, the electronic message may include one of a short messaging service (SMS) message, an instant messenger message, an email, an audible alert on a remote programmer, a visual alert on a remote programmer, an audible alert on a wireless device, a visual alert on a wireless device, and the like.

Delivering therapy to the patient, another fail-safe operation, includes therapy delivered via one of an automated external defibrillator (AED), a drug pump, an implantable monitor, a neurostimulator, IMD 12, and the like. For example, IMD 12 may deliver appropriate therapy via therapy interface 42 upon detection of an adverse event from failure detection module 38. A diagnostic interface 40 may sense physiological conditions from a patient and/or IMD 12 for diagnosing therapy. Diagnostic interface 40 sends the physiological conditions to processor 36, which determines an appropriate therapy according to the conditions. In this case, IMD 12 overrides new program parameters 48 if an adverse event, such as an inappropriate device operation or patient response, is detected.

In another embodiment, therapy interface 42 is coupled to an external device, which delivers therapy to a patient. For example, an AED may be integrated with or coupled to local programmer/monitor 14 to monitor patient data, such as an electrocardiogram (ECG), and provide therapy if IMD 12 is not already providing appropriate therapy. Another example of delivering therapy may include a drug pump that is directed to release a prescribed amount of a medication in accordance with a detected adverse event. Alternatively, instructions may be given to indicate the suggested therapy that the patient should undergo. In each case, processor 36 controls telemetry interface 44 for communication with the external therapy device, either directly or indirectly via local programmer/monitor 14, to request delivery of therapy.

Figure 4:
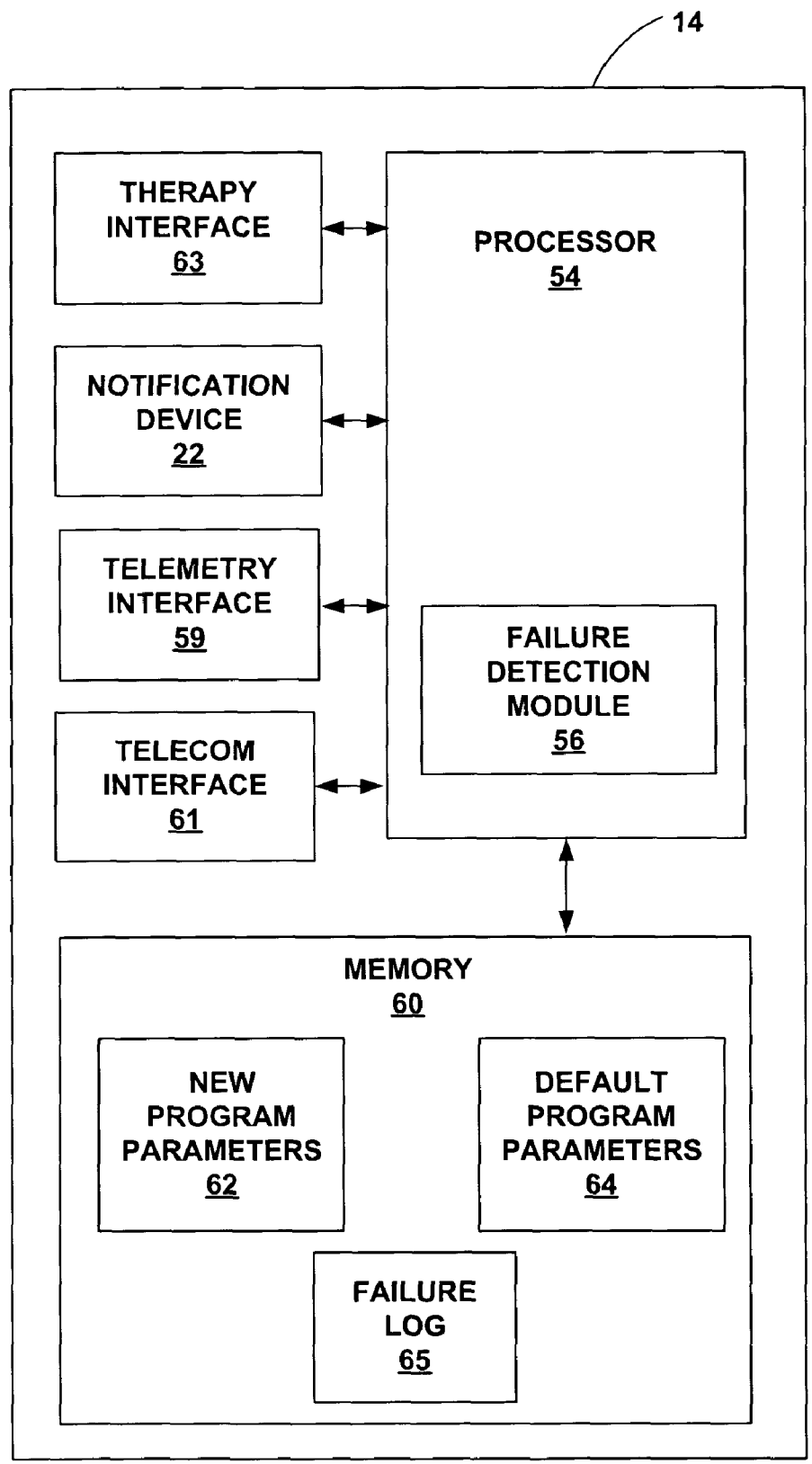
FIG. 4 is a conceptual diagram illustrating an exemplary local programmer/monitor that provides fail-safe operations if an adverse event occurs.

FIG. 4 is a conceptual diagram illustrating an exemplary local programmer/monitor 14 that provides fail-safe operations if an adverse event associated with remote programming occurs. As shown in FIG. 4, local programmer/monitor 14 includes a processor 54 that executes a failure detection module 56 to detect an adverse event, such as a programming session failure between telemetry interface 59 and IMD 12, or between a telecommunication interface 61 and remote programmer 18. In response to detection of an adverse event, processor 54 invokes an appropriate fail-safe operation, such as notifying a person concerning the failure of the programming session via a notification device 22, modifying programming parameters within the implantable medical device, and delivering a therapy to a patient. Any combination of these fail-safe operations may be used.

As further shown in FIG. 4, local programmer/monitor 14 may include a therapy interface 63 to control delivery of therapy from an external therapy device such as an AED, neurostimulator or drum pump. Also, in some embodiments, a failure log 65 may be updated if a programming session fails. Failure log 65 may provide information about the weaknesses of programming session connections. Failure log 65 may include other information, such as information describing therapy that has been delivered. In one embodiment, the information logged by failure log 53 may be sent to a device such as remote programmer 18.

In some embodiments, a memory 60 buffers new program parameters 62 received in the course of a remote programming session and default program parameters 64. In the event an adverse event is detected, processor 54 extracts default program parameters 64 from memory 60 and transmits them to IMD 12. Alternatively, if the remote programming session is successful, processor 54 transmits the new program parameters 62 to IMD 12 to program the IMD.

Thus, in the example of FIG. 4, new program parameters can be buffered and accumulated, and then transmitted only if the remote programming session with remote programmer 18 was successful. Even after the new program parameters 62 are transmitted to IMD 12, processor 54 of local programmer/ monitor 14 may send default program parameters 64 if inappropriate operation or patient response is detected from IMD 12, e.g., in a case where IMD 12 notifies local programmer/monitor 14 of inappropriate operation or patient response. Hence, FIG. 4 represents an alternative to storage of default parameters within IMD 12, as in the example of FIG. 3.

Figure 5:
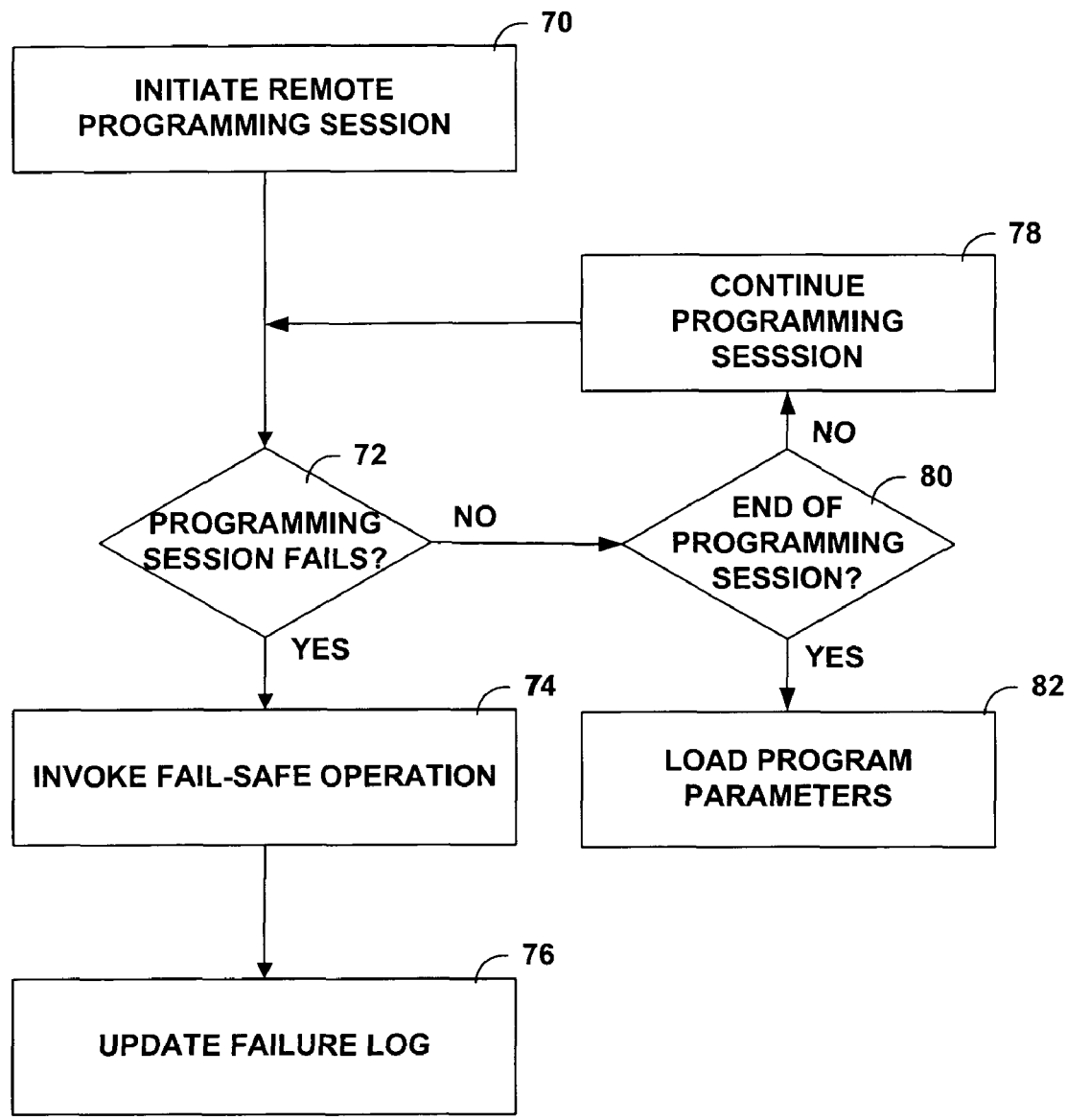
FIG. 5 is a flow diagram illustrating remote programming of an implantable medical device (IMD) with exemplary fail-safe functionality.

FIG. 5 is a flow diagram illustrating remote programming of an implantable medical device (IMD) 12 with exemplary fail-safe functionality. As shown in FIG. 5, a remote programming session is initiated to send programming parameters (70), e.g., by a remote programmer 18. Remote programmer 18 communicates with local programmer/monitor 14 via network 16 to conduct the remote programming session. In the course of the remote programming session, remote programmer 18 sends parameters to IMD 22 via local programmer/monitor 14. IMD 12, remote programmer 18, or local programmer/monitor 14 detects whether the programming session fails (72).

The programming session may fail for a number of reasons. For example, there may be a disruption in telemetry between IMD 12 and local programmer 14 located proximate IMD 12. Alternatively, there may be a disruption in a telecommunication link between the local programmer 14 and remote programmer 18. It is also possible that the programming session may fail due to a loss of connection between clinician instrumentation and remote programmer 18, or due to a loss of a network connection. The programming session may also fail if any initialization instructions or programming parameters were corrupted.

In the event the programming session fails (72), a fail-safe operation is invoked (74), e.g., by IMD 12, local programmer/monitor 14, or remote programmer 18, as described herein. In one embodiment, a failure log may be updated (76) after a programming session fails. The failure log may provide information about the weaknesses of programming session connections. In addition, the failure log may include other information, such as information describing therapy that has been delivered.

In one embodiment, the information logged by failure log 53 may be sent to a device such as remote programmer 18. If the programming session does not fail and the programming session is not complete (80), then the programming session will continue (78) until it fails or ends. If the programming session does not fail and the programming session is not complete (80), then program parameters from the programming may be loaded into IMD 12 (82).

Figure 6:
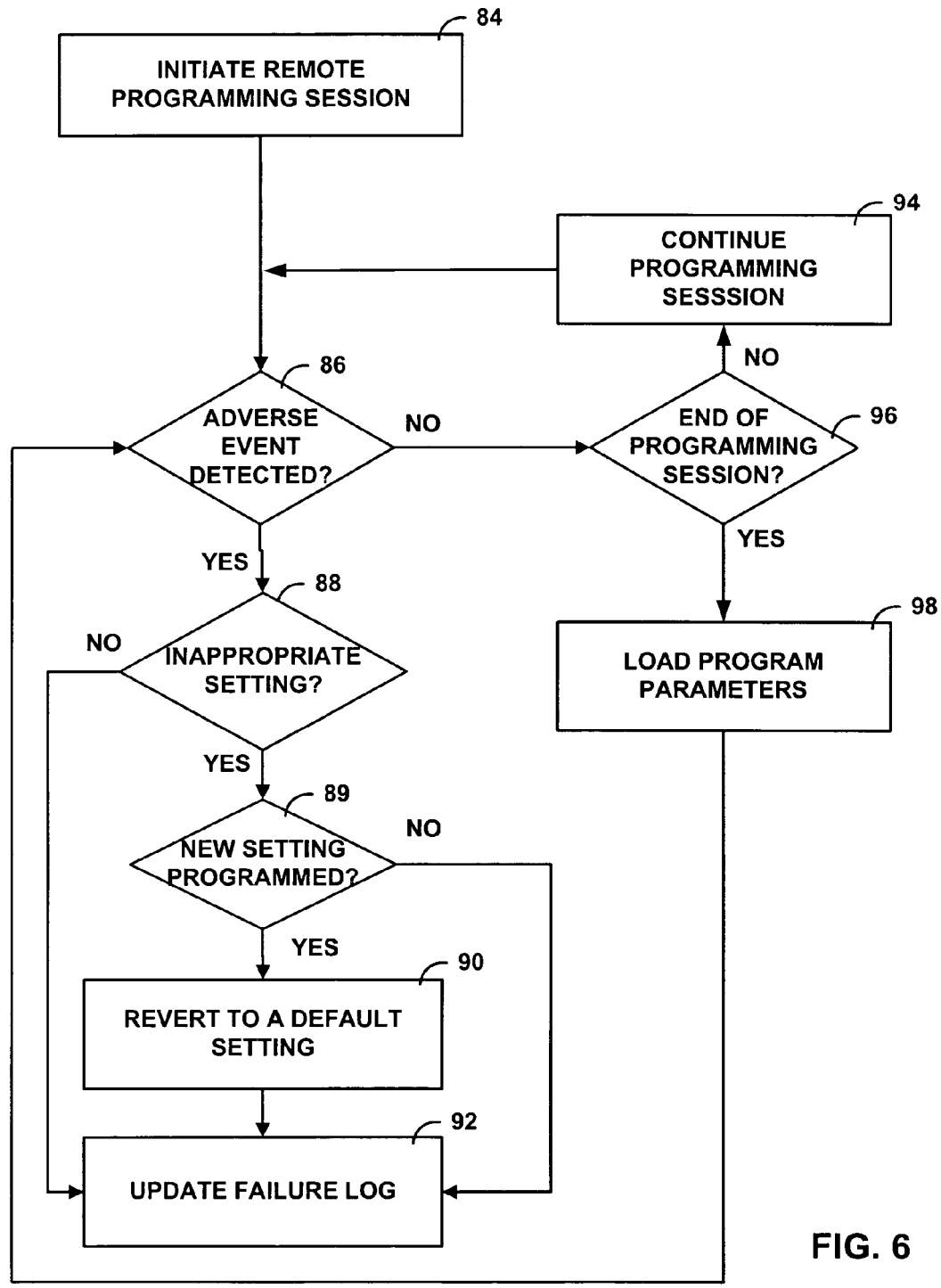
FIG. 6 is a flow diagram illustrating remote programming of an implantable medical device (IMD) with exemplary fail-safe functionality.

FIG. 6 is a flow diagram illustrating remote programming of an implantable medical device (IMD) with exemplary fail-safe functionality. As shown in FIG. 6, a remote programming session is initiated to send programming parameters (84). IMD 12 or local programmer/monitor 14 then detects whether an adverse event has occurred (86). Again, an adverse event may include one of a programming session failure, inappropriate device behavior, and inappropriate patient response.

Inappropriate device behavior may comprise one of an asystole by IMD 12, inappropriate IMD sensitivity settings, inappropriate AV delay settings, inappropriate pacing and defibrillation output settings, inappropriate refractory period settings, and the like. Inappropriate patient response may include low pacing outputs, low pacing rate, loss of capture, loss of sensing or monitoring, loss of defibrillation efficacy, arrhythmia, and the like.

In the event an adverse event is detected (86), it may be determined that the programming parameter setting for IMD 12 is inappropriate (88). However, the occurrence of adverse event may not necessarily mean a setting is programming parameter inappropriate. If an adverse event is detected but the programming parameter setting is still appropriate, then the setting will not be changed. If an adverse event is detected, the programming parameter setting is determined to be inappropriate, the programming parameter setting has been programmed (89) then IMD 12 may direct one or more parameters to revert to a default parameter setting (90).

For example, IMD 12 may load the default parameters into control register 52 (FIG. 3). Alternatively, IMD 12 may set a parameter to a setting of a "safe mode" setting within a safety range determined for the IMD and the patient. If the setting had not yet been programmed, it may not be necessary to revert to a default setting or enter into a "safe mode". In one embodiment, a failure log may be updated (92) after an adverse event is detected. The failure log may provide information about the weaknesses of programming session connections. As indicated above, the failure log may include other information, such as information describing therapy that has been delivered. In one embodiment, the information logged by failure log 53 may be sent to a device such as remote programmer 18.

If the adverse event is not detected and the programming session is not complete (96), then the programming session will continue (94) until it ends or an adverse event is detected. If the adverse event is not detected and the programming session is complete (96), then program parameters from the programming may be loaded into IMD 12 (98). After running with the program parameters, IMD 12 may be monitored again to detect an adverse event.

Various embodiments of the invention have been described. These and other embodiments are within the scope of the following claims.

The invention claimed is:

1. A method comprising:
    initiating a remote programming session within an implantable medical device over a long-range telecommunication link, the remote programming session comprising providing signals from a programming device separate and remote from the implantable medical device to program the implantable medical device with operating parameters defining operation of the implantable medical device, the remote programming device being at a site located a significant distance from the implantable medical device;
    in the event the remote programming session succeeds, operating the implantable medical device according to the operating parameters following the remote programming session; and
    invoking a fail-safe operation in the event the remote programming session fails, wherein invoking the fail-safe operation includes automatically modifying the operating parameters of the implantable medical device and operating the implantable medical device according to the modified operating parameters following the failed remote programming session.

2. The method of claim 1, wherein invoking the fail-safe operation includes notifying a person concerning the failure of the programming session.

3. The method of claim 2, wherein notifying a person includes generating an alarm from within the implantable medical device.

4. The method of claim 3, wherein generating an alarm from within the implantable medical device comprises generating one of a vibration and a sound.

5. The method of claim 2, wherein notifying a person comprises sending an electronic message to the person.

6. The method of claim 5, wherein the electronic message includes one of a short messaging service (SMS) message, an instant messenger message, an email, an audible alert on a remote programmer, a visual alert on a remote programmer, an audible alert on a wireless device, and a visual alert on a wireless device.

7. The method of claim 1, wherein modifying the operating parameters includes waiting for a delay period following the failed programming session before modifying the operating parameters.

8. The method of claim 1, wherein operating the implantable medical device according to the modified operating parameters comprises delivering a therapy to a patient based on the modified operating parameters via one of an automated external defibrillator (AED), a drug pump, a neurostimulator, and the implantable medical device.

9. The method of claim 1, wherein the implantable medical device includes one of a cardiac pacemaker, a neurostimulator, and a drug pump.

10. The method of claim 1, wherein providing signals from a programming device separate and remote from the implantable medical device to program the implantable medical device comprises:

transmitting first signals from the remote programming device to a local programmer; and transmitting second signals from the local programmer to the implantable medical device.

11. The method of claim 10, wherein the first signals are transmitted via the Internet.

12. The method of claim 1, wherein modifying the operating parameters comprises reverting to default operating parameters.

13. The method of claim 1, wherein modifying the operating parameters comprises restoring a previous operating parameter setting.

14. The method of claim 1, wherein operating the implantable medical device according to the first operating parameters comprises delivering therapy to the patient according to the first operating parameters.

15. The method of claim 1, wherein operating the implantable medical device according to the first operating parameters comprises monitoring one or more patient parameters according to the first operating parameters.

* * * * *